US 6,583,617 B2

(12) United States Patent
LeVert et al.

(10) Patent No.: US 6,583,617 B2
(45) Date of Patent: Jun. 24, 2003

(54) BARKHAUSEN NOISE MEASUREMENT PROBE WITH MAGNETORESISTIVE SENSOR AND CYLINDRICAL MAGNETIC SHIELD (75) Inventors: Gerald C. LeVert, Knoxville, TN (US); Francis E. LeVert, Knoxville, TN (US)

(73) Assignee: Kemp Corporation, Knoxville, TN (US)

( * ) Notice: Subject to any disclaimer, the term of this patent is extended or adjusted under 35 U.S.C. 154(b) by 0 days.

(21) Appl. No.: 09/940,212

(22) Filed: Aug. 28, 2001

(65) Prior Publication Data
US 2002/0024337 A1 Feb. 28, 2002

Related U.S. Application Data
(60) Provisional application No. 60/227,265, filed on Aug. 24, 2000.

(51) Int. Cl.[7] .............. G01N 27/72; G01R 33/09; G01R 33/12; G01B 7/24
(52) U.S. Cl. .............. 324/235; 324/209; 324/242
(58) Field of Search .............. 324/209, 225, 324/235, 239–243

(56) References Cited

U.S. PATENT DOCUMENTS

| 5,313,405 | A | * | 5/1994 | Jiles et al. ............. 324/209 |
| 5,619,135 | A | * | 4/1997 | Kohn et al. ............ 324/239 |
| 5,828,211 | A | * | 10/1998 | Scruby et al. .......... 324/209 |
| 6,150,809 | A | * | 11/2000 | Tiernan et al. ......... 324/235 X |

FOREIGN PATENT DOCUMENTS

DE          253685     *  1/1988  ............. 324/209

* cited by examiner

Primary Examiner—Gerard R. Strecker (57) ABSTRACT

A Barkhausen probe includes a magnetizing field generator, a magnetoresistive magnetic field sensor, a direct current power supply for biasing the magnetoresistive magnetic field sensor and signal conditioning electronics. The Barkhausen probe is capable of generating and sensing the Barkhausen noise emanating from the surface of a cyclic magnetized specimen. The conditioned Barkhausen noise output of the signal conditioning electronics is usable as input to various analysis systems where textural analysis of the material can be performed.

16 Claims, 7 Drawing Sheets

BARKHAUSEN NOISE MEASUREMENT PROBE WITH MAGNETORESISTIVE SENSOR AND CYLINDRICAL MAGNETIC SHIELD

CROSS REFERENCE OF RELATED APPLICATIONS

Pursuant to 35 U.S.C. Section 119, the benefit of priority from Provisional Application No. 60/227,265 with filing date Aug. 24, 2000 is claimed for this Non-Provisional Application.

BACKGROUND OF THE INVENTION

1. Technical Field of the Invention

The present invention relates generally to a probe for detecting the Barkhausen signals from a ferromagnetic sample when it is exposed to a varying external magnetic field.

2. Background and Objects of the Invention

The Barkhausen noise method is based on the concept of ferromagnetic domains. Each domain is magnetized along a certain crystallographic easy direction of magnetization. Domains are separated from one another by walls within which the direction of the magnetization vectors usually turns 180 or 90 degrees. When a magnetic field or mechanical stress is applied to a ferromagnetic material, changes take place in its domain structure by abrupt movement of domain walls or rotation of domain magnetization vectors. The abrupt movements of the domain walls result in step changes in the magnetization curve of a ferromagnetic material that can be observed by sensitive measurements. If a coil of conducting wire is placed near a ferromagnetic material while its domain walls are moving, the resulting change in the magnetization of the ferromagnetic material will induce electrical pulses in the coil. These electrical pulses, which are stochastic in nature, make up what is called Barkhausen noise. The frequency content of the Barkhausen noise gives rise to a power spectrum that will start at the magnetizing frequency and extend up to several megahertz. The magnetic signals are exponentially damped as a function of the distance they have to travel from within the material to its surface. The magnetic pulses undergo damping due to counter magnetic fields set up within the material by transient eddy currents. The amount of damping determines the depth from which information can be obtained. The operating frequency of a Barkhausen noise probe is a function of its type, size and geometry. It is an object of this invention to provide a Barkhausen noise probe that has high sensitivity at very low frequencies.

Sakamoto et al., in U.S. Pat. No. 6,073,493 described a Barkhausen apparatus with a U-shaped magnetic excitation head and a magnetic detection head consisting of a wire wound air-core coil. The U-shaped excitation head is made of soft magnetic material and an excitation coil. The apparatus of Sakamoto is designed to diagnose the fatigue life structural steel work using the root-mean-square (RMS) voltage or voltage amplitude value of the Barkhausen noise.

Kohn et al., U.S. Pat. No. 5,619,135 described a steel hardness measuring system that comprises an energizing yoke, a Hall probe, a Barkhausen signal sensor and a signal processing unit. The coil-wound energizing yoke is used to provide the magnetic flux to generate the Barkhausen noise within the sample. The Hall probe was provided to measure the tangential magnetic field intensity H at the surface of the sample to provide for calibrations of the device of U.S. Pat. No. 5,619,135. The Barkhausen signal sensor in this case was of one of a variety of known coil type sensors designed to sense a changing magnetic flux. The invention of this utility patent application has only to do with the probe for creating and detecting the Barkhausen noise.

Perry, in U.S. Pat. No. 5,166,613 invented a system for identifying and measuring stress at specific locations within a ferromagnetic material by the production and detection of Barkhausen noise during magnetization of the material. The apparatus of Perry consists of a signal generator for generating a combined cyclic and spatially varying magnetic field signal using two electromagnets located on opposing faces of a sample. He teaches the use of acoustical Barkhausen noise sensors located near the two electromagnets coupled to computing and analysis capability for analyzing the acoustic Barkhausen noise. The acoustic sensors, which must be attached to the sample, are designed to operate in the frequency range from 75 to 450 kHz. These sensors provided for greater penetration into the thickness of a test sample than what is normally associated with wound coils. The aim of this invention is to provide a probe that will provide for the sensing of Barkhausen noise from depths not possible with the typical wire wound coils. A still further aim is to provide a sensor that will not have to be physically attached to the surface of a test sample.

Typically the sensor used to detect Barkhausen noise may comprise any of a variety of known coil sensor types. Examples of prior art Barkhausen signal sensors include encircling coils, surface pancake coils, ferrite core surface coils, etc. All detection coils are based upon Faraday's Law, which states that the total emf induced in a closed circuit, is equal to the time rate of decrease of the total magnetic flux linking the circuit. That is, the induced emf is a function of the area of the coil and the rate of change of the magnetic flux at the coil. This suggests that a wire wound coil has reduced sensitivity at low frequencies. It is an object of this invention to provide a Barkhausen noise generator and detector with increased sensitivity at lower frequencies. It is a further object to provide a Barkhausen generating and sensing probe that can sample a ferromagnetic material at depths not available with coil-based Barkhausen noise detectors. It is an additional object of this invention to provide a Barkhausen probe that can be used with commonly available signal conditioning and analysis systems to measure residual stress, detect faults in structures and other material properties. Other objects of the probe of this invention will become obvious during the course of the description of the probe.

OTHER REFERENCES

Pasley, R., Barkhausen Effect—An Indication of Stress, Material Evaluation, Vol. 28, No 7, July 1970, pp. 157–161.

Dhar, A., Jagadish, C., and Atherton, D. L., Using the Barkhausen Effect to Determine the Easy Axis of Magnetization in Steels, Material Evaluation, October 1992, pp. 1139–1141.

Francino, P., and Tiitto, K., Evaluation of Surface and Subsurface Stresses with Barkhausen Noise: A Numerical Approach, Practical Applications of Residual Stress Technology, Proceedings of the Third International Conference, Indianapolis, Ind. May 15–17, 1991.

SUMMARY OF THE INVENTION

A Barkhausen probe comprising: a magnetizing fields generator; a magnetoresistive magnetic field sensor; a direct current power supply for biasing the magnetoresistive magnetic field sensor; and signal conditioning electronics is described. The Barkhausen probe is capable of generating and sensing the Barkhausen noise emanating from the surface of a cyclic magnetized specimen. The conditioned Barkhausen noise output of the signal conditioning electronics is usable as input to various analysis systems.

DETAILED DESCRIPTION OF THE PREFERRED EMBODIMENTS

Several preferred embodiments of the present invention will be described below with reference to the accompanying figures.

First Embodiment

Figure 1:
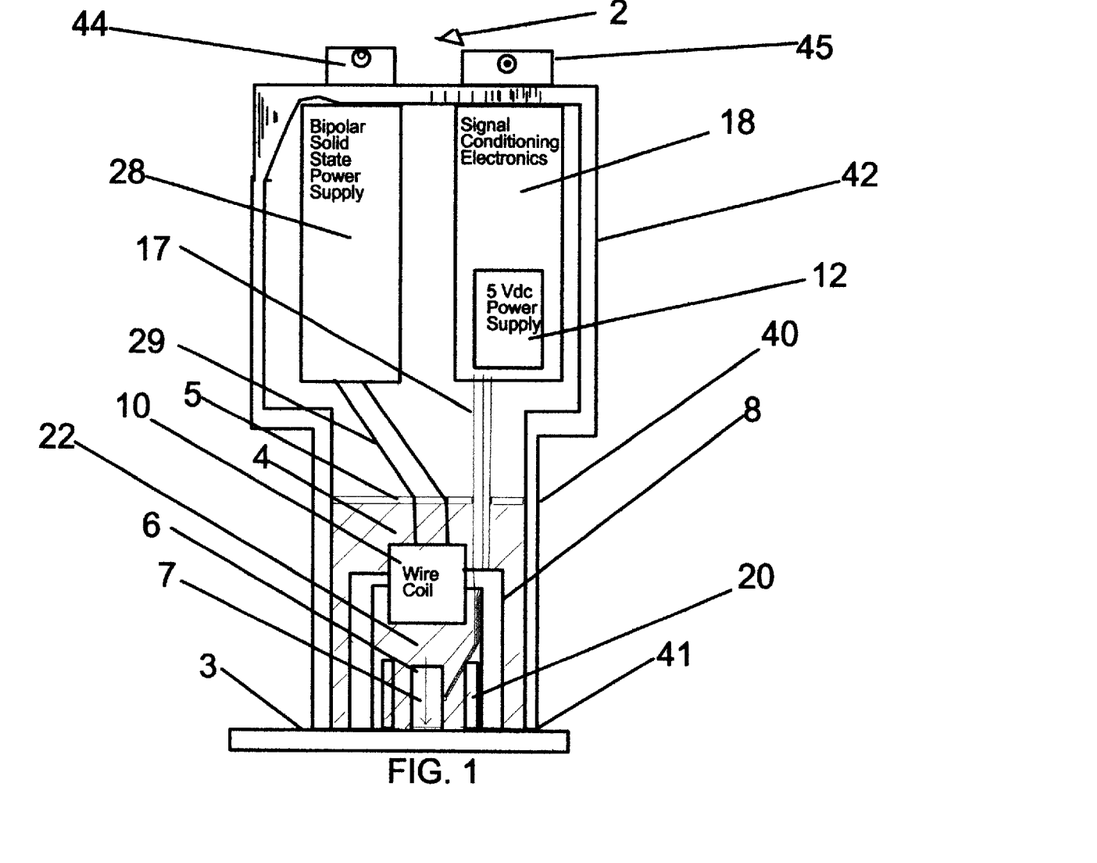
FIG. 1 is a sketch showing a schematic representation of a side view of the Barkhausen probe of the first embodiment of this invention with its sensitive axis essentially perpendicular to the surface of the test specimen.

The first embodiment will now be described. The first embodiment of the device of this invention is schematically represented in FIG. 1. As shown in FIG. 1, the Barkhausen probe is indicated generally by the numeral 2. The Barkhausen probe 2 comprises magnetic excitation head 4 and magnetoresistive material based Barkhausen noise pickup sensor 6 with its sensitive axis 7 having a direction that is substantially perpendicular to the surface of test sample 3. The magnetic excitation head 4 (hereafter referred to as electromagnet 4) has U-shaped core 8 made of soft or easily magnetized material. The U-shaped core 8 of electromagnet 4 may consist of laminated transformer steel such as grain oriented silicon steel or any material that has good magnetic permeability and sufficiently high magnetic saturation. The electromagnet 4 is formed with electrically insulated wire (e.g. enamel transformer wire) 10 coiled around the U-shaped core 8. Materials such as mu-metal or an amorphous magnetic material can also be used to make sufficiently adequate core materials.

Figure 2:
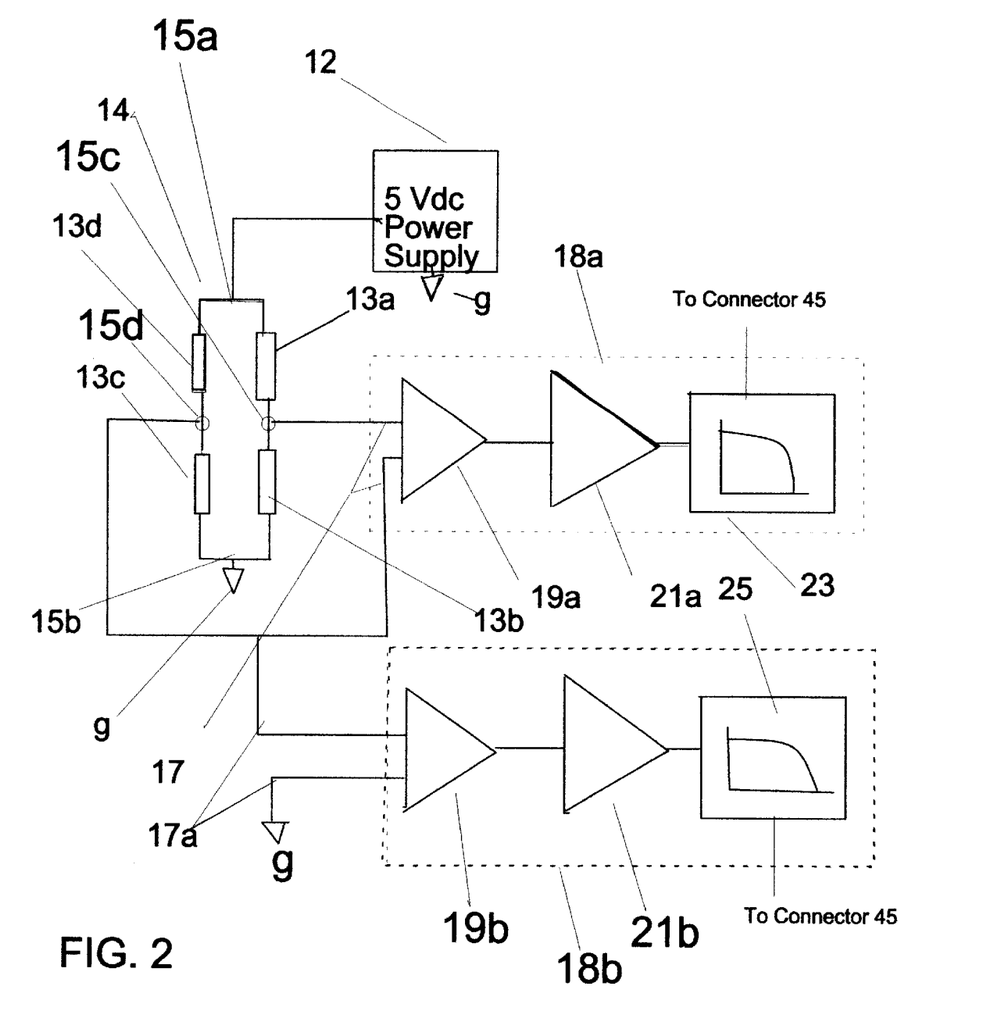
FIG. 2 is a sketch showing a schematic representation of the Barkhausen noise detector and signal conditioning electronics of the probe of the first embodiment of the invention.

Pickup sensor 6, which is a commercially available solid-state device, comprises four magnetoresistive elements 13a, 13b, 13c and 13d configured in a solid-state Wheatstone bridge configuration (WBC) 14 as shown schematically in FIG. 2. Magnetoresistive elements 13a and 13c are designed to respond to transient or steady state magnetic signals while elements 13b and 13d are magnetically shielded from magnetic fields of all types. Nodes 15a and 15b of the Wheatstone bridge 14 are connected to the positive and ground terminals, respectively, of ordinary 5 volt power supply 12 of FIGS. 1 and 2. The output voltage of the solid-state bridge circuit WBC 14 is sensed at the two opposing nodes 15d and 15c, which are connected to channel 18a of signal conditioning electronics 18 as shown schematically in FIG. 2. The signal conditioning electronics 18 is composed of channel 18a and 18b as shown in FIG. 2. The pickup sensor 6 (see FIGS. 1 and 3) is, as mentioned before, a solid-state representation of WBC 14 FIG. 2. The elements of the Wheatstone bridge 14 are not very sensitive to magnetic fields whose directions are not parallel to the easy axis 7 of the solid-state bridge circuit (see FIG. 1). Even though the WBC 14 offers certain advantages for detecting fluctuating signals, a single element giant magnetoresistive sensor could be used for detecting Barkhausen noise signals. Further, the intensity of the magnetic field proximate the surface of test sample 3 can be monitored by recourse to electrical connections between nodes 15d and 15b (see FIG. 2). In the Wheatstone bridge configuration of FIG. 2, as mentioned previously, the elements 13a and 13c are exposed to the Barkhausen generated noise while the remaining two elements, 13b and 13d are shielded from all external magnetic fields. When an external field is applied to sensor 6, the exposed elements 13a and 13c undergo decreases in their electrical resistance, causing a potential difference between bridge nodes 15c and 15d. Hence, if the bridge circuit of FIG. 2 is powered, as shown, by 5 Vdc supply 12, the voltage drop across element 13c is directly proportional to the Barkhausen noise (i.e., magnetic field pulses) generated within a ferromagnetic sample and indirectly related to the intensity of the incident magnetic field. Therefore, it is possible to simultaneously monitor the Barkhausen noise being generated and to estimate the intensity of the applied magnetic field by monitoring the voltage between node 15d and ground (i.e., node 15c).

Figure 3:
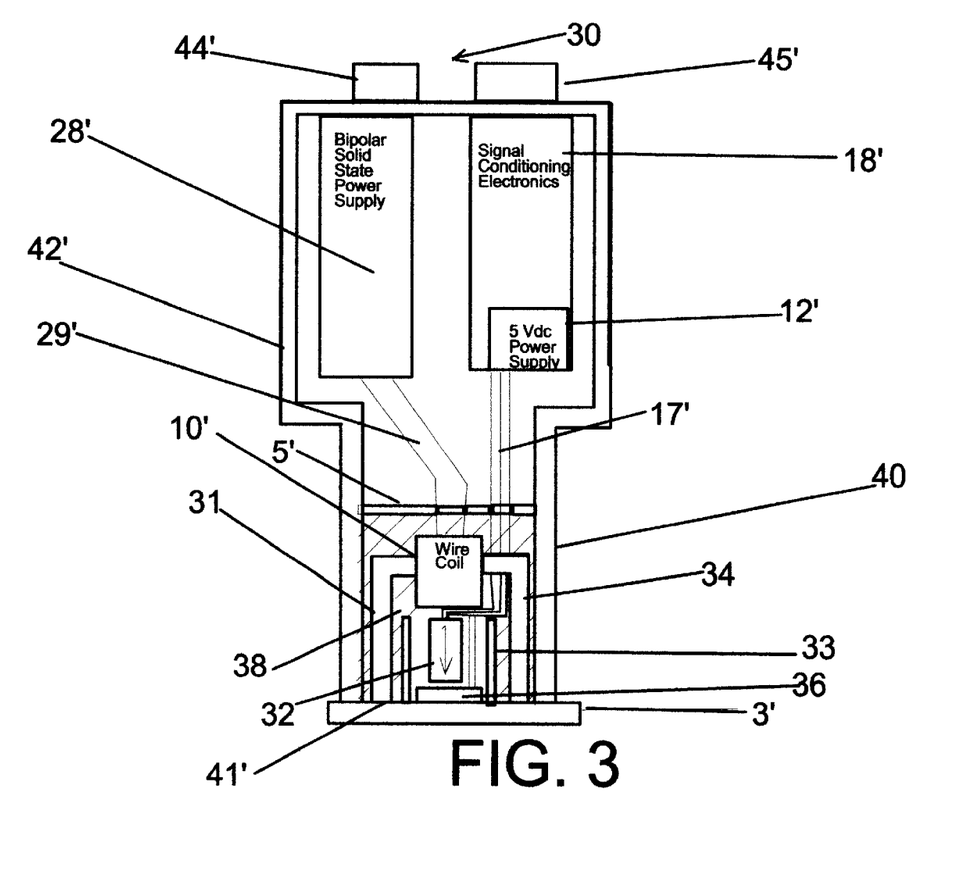
FIG. 3 is a sketch showing a schematic representation of the probe of second embodiment of this invention
Figure 4:
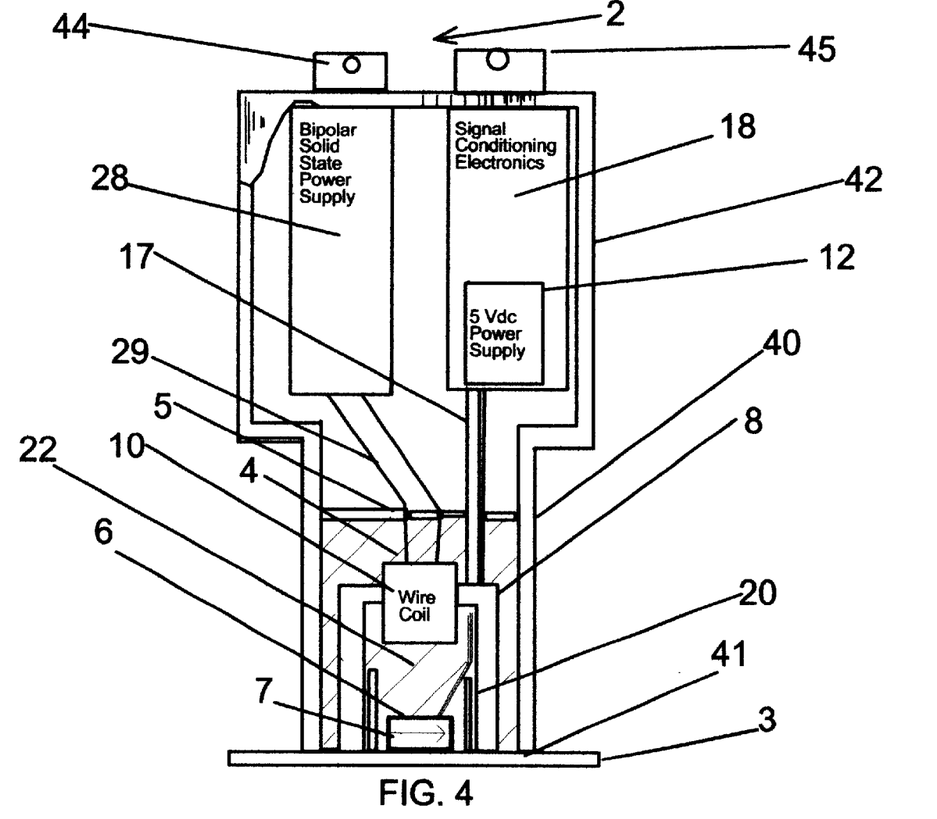
FIG. 4 is a schematic representation of a side view of the probe of the first embodiment of this invention with the sensitive axis of the Barkhausen noise sensor essentially parallel to the surface of the test specimen.
Figure 5:
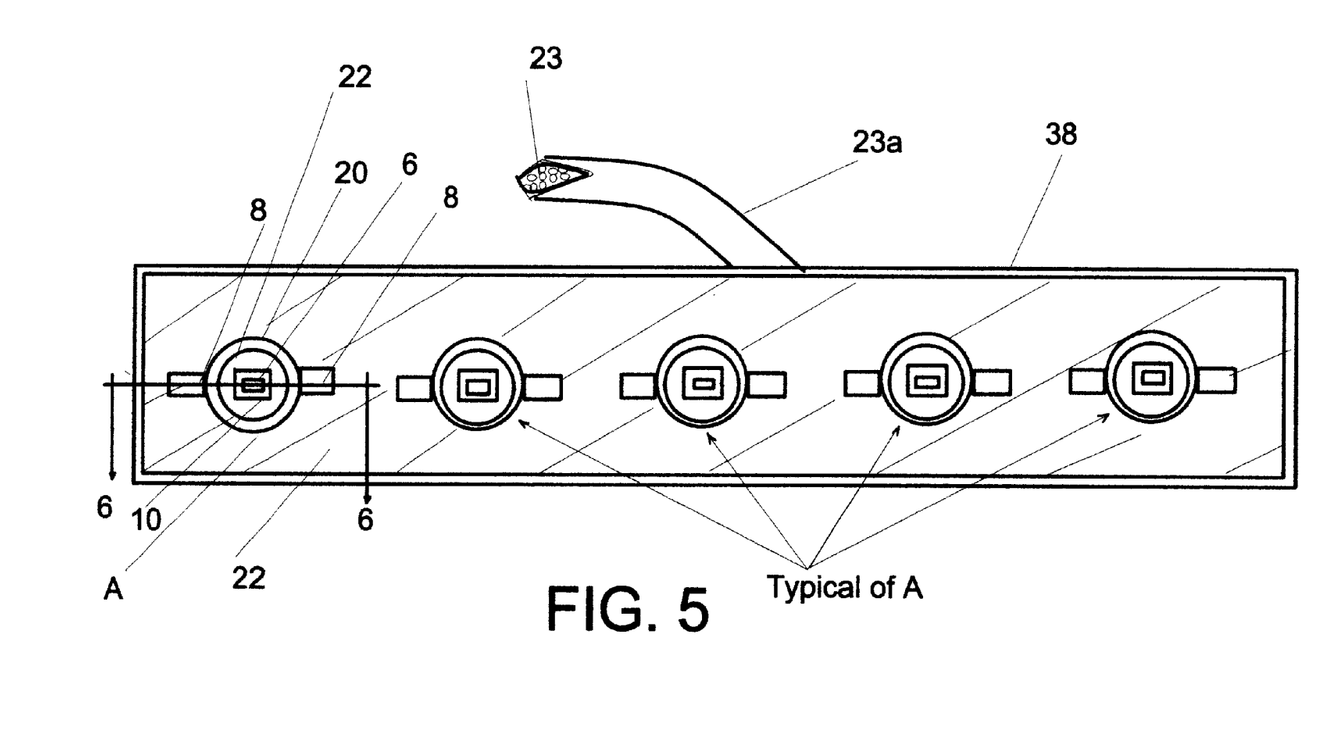
FIG. 5 is a bottom view of a multiplicity of Barkhausen probes arrayed in an integral housing.
Figure 6:
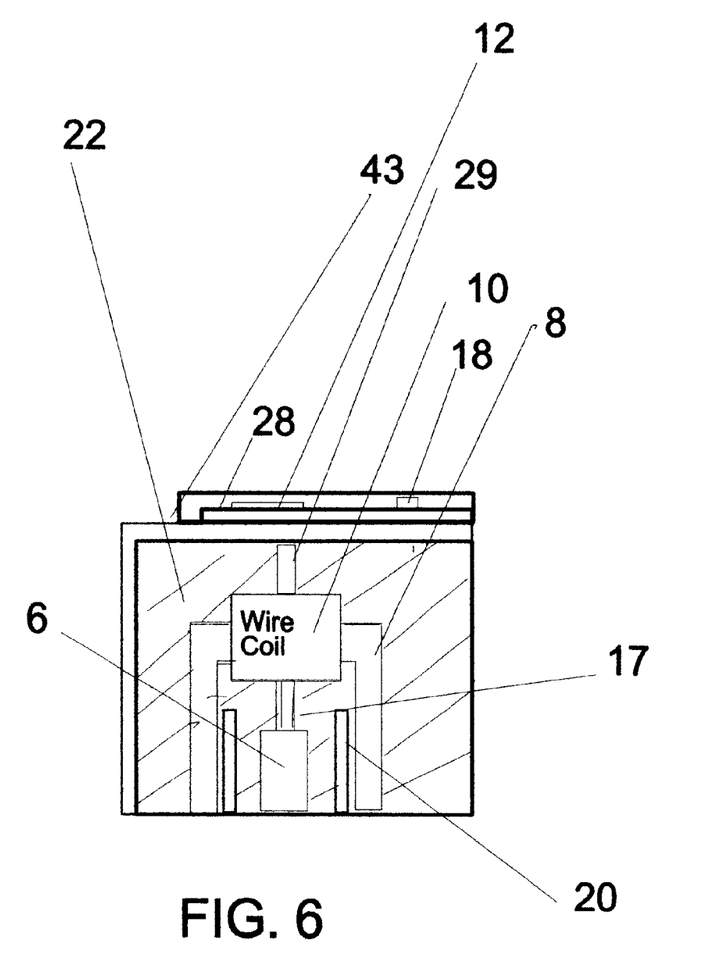
FIG. 6 is a cross sectional side view of one of the multiplicity of Barkhausen probes of FIG. 5.

The sensitive axis 7 of sensor 6 is positioned so as to be substantially perpendicular to the surface of test specimen 3 and is collinear with the central vertical axis of cylindrical sleeve 20. The cylindrical sleeve 20 can be used to provide magnetic field shielding for sensor 6 and to ensure the position of sensor 6 in regards to its symmetrical location at the first terminal end 41 of tube 40. The cylindrical sleeve 20 of FIG. 1 is made of dielectric material. It could, however, have been made of mu-metal or other magneticfield shielding materials. When the cylindrical sleeve 20 is made of mu-metal, it forms a barrier against magnetic fields and hence substantially reduces the strength of fluctuating and non-fluctuating magnetic fields at the location of sensor 6 whose directions are not substantially perpendicular to the surface of the specimen to which the Barkhausen probe is applied in non-destructive testing. The WBC 14 or sensor 6 is inserted into sleeve 20 such that its central vertical axis is collinear with the vertical axis of cylindrical sleeve 20. The air filled volume of probe 2 bounded by a plane that is coplanar with the first terminal end 41 of tube 40 and disk 5 is filled with potting compound 22 as shown in FIGS. 1, 3 and 4. The magnetic excitation head 4 and the pickup sensor 6, which can be made very small because of the solid-state nature of the pickup sensor 6, are potted in dielectric potting compound 22. The active end of the probe could be made even smaller using hybrid circuitry where the excitation head 4, pickup sensor 6 and signal conditioning electronics 18 are packaged using hybrid and integrated circuitry technology (see FIGS. 5 and 6). In FIG. 5, a multiplicity of magnetic field excitation heads 4, cylindrical sleeves 20 and Barkhausen noise sensors 6 are potted in potting compound 22 identical to that used in the probes of FIGS. 1, 3, and 4. The aggregate is housed in plastic housing unit 38 thereby forming an array of sensors for use in non-destructive material testing. The signal conditioning electronics 18 (not shown in FIG. 5) are shown schematically in the cross sectional view of FIG. 6. In FIG. 5, the outputs from the array of Barkhausen probes are fed from the signal conditioning electronics, such as that shown in FIG. 2, to a multi-input analysis unit (not shown) via multiple pairs of electrical leads 23 bundled together in sheath 23a (see FIG. 5).

A single probe of this invention, such as that shown in FIG. 1, has an overall diameter of approximately 12.5 mm at its active end. The die of pickup sensor 6 can be made with volumes less than 0.5 mm×0.5 mm×0.75 mm. When made using hybrid and integrated circuitry technology, probes smaller than 4 mm will be possible. A very small probe would make the use of the Barkhausen noise technique applicable in measurement applications where the space or volume required for insertion of a probe is limited. Also, a miniaturize probe would provide for good spatial resolution The probe will be usable on components with small radiuses of curvature as is found in many components of high performance engines. While the magnetic field sensor of the Barkhausen probe 2 is made of magnetoresistive elements in a Wheatstone bridge configuration it could, however, been made of anisotropic magnetoresistive or Giant magnetoresistive materials in Wheatstone bridge configuration.

The signal conditioning circuitry 18, which is composed of dual electronic channels 18a and 18b, is shown in box representation in FIG. 1 and schematically in FIG. 2. Channel 18a comprises commercially available ordinary instrumentation amplifier 19a whose dual input is connected to nodes 15c and 15d of WBC 14 via electrical leads 17, low noise high gain bandwidth amplifier 21a with its input connected to the output of instrumentation amplifier 19a, and bandpass filter 23 whose input is connected to the output of low noise high gain bandwidth amplifier 21a. The output of bandpass filter 23 is electrically connected to connector 45 of FIG. 1. Channel 18b consists of instrumentation amplifier 19b whose dual input is connected to node 15d and ground via electrical leads 17a, low-noise high gain bandwidth amplifier 21b with its input connected to the output of instrumentation amplifier 19b, and lowpass filter 25 whose input is electrically connected to the output of amplifier 19b and whose output is connected to connector 45 of FIG. 1. The bandpass filter 23 and the lowpass filter 25 were selected from commercially available units that, like the instrumentation and low noise amplifiers, avoided the use of components with ferromagnetic constituent parts. The active integrated circuit components may be powered by dual or single sided power supplies such as the 5 Vdc supply 12. The bipolar solid-state power supply 28 of FIGS. 1 and 3, which is electrically coupled to electromagnet 4 as by electrical leads 29, is also electrically connected to t connector 44. The first end of Barkhausen probe 2 is housed in cylindrical tube 40. The handheld portion of Barkhausen probe 2 consists of cylindrical tube 42. During a measurement, the first terminal end 41 of cylindrical tube 40 is essentially in mechanical contact with specimen 3.

FIG. 4 shows a side view of the device of the first embodiment of the invention shown in FIG. 1 wherein the pickup sensor 6 is deployed with the direction of its sensitive axis 7 normal or orthogonal to the inner surface of tube 40. In this configuration, with sleeve 20 made of dielectric material, the most sensitive orientation of the probe 2 during use is with the central vertical axis of tube 40 turned 90° away from a normal to the surface of a specimen.

The probe of this patent application is designed to be operated at frequencies between a few Hz and several hundreds Hz. For example, during the course of the development of this invention the probe was operated between 5 Hz and 5000 Hz. The output pulse rate of the Barkhausen noise pulses are of the order of thousands per second as the domain flips from one direction of easy magnetization to another. The theoretical energy content of these pulses is almost uniform from essentially zero Hz up to several MHz. However, when the Barkhausen noise is Fourier transformed to obtain a frequency spectrum, the signal intensity generally decreases with an increase in frequency. The detection efficiency is then related to the bandwidth of the Barkhausen signal used in the analysis.

Second Embodiment

The probe of the second embodiment will now be described. The second embodiment of the device of this invention is schematically represented in FIG. 3. As shown in FIG. 3, the Barkhausen probe of the second embodiment is indicated generally by the numeral 30. The Barkhausen probe 30 comprises magnetic excitation head 31 and magnetoresistive magnetic field sensor 32. The magnetic excitation head 31 (hereafter referred to as electromagnet 31) has U-shaped core 34 made of soft or easily magnetized material. The U-shaped core 34 of electromagnet 31 may consist of laminated transformer steel such as grain-oriented silicon steel or any material that has good magnetic permeability and sufficiently high magnetic saturation. The electromagnet 31 is formed with electrically insulated wire (e.g. enamel transformer wire) 10 coiled around the U-shaped core 34. Juxtaposed next to magnetoresistive magnetic field sensor 36 with its easy axis in a plane perpendicular to the plane containing the vertical axis of the magnetoresistive magnetic field sensor 36 is solid-state magnetic field sensor 32, which is used to monitor changes in the intensity of the applied magnetic field proximate the surface of test specimen 3'. The giant magnetoresistive magnetic field sensor 36 performs the same function as the pickup sensor 6 of the first embodiment of this invention. That is, it acts as a Barkhausen noise detector. The giant magnetoresistive magnetic field sensor 36 could be made in a Wheatstone bridge configuration. The magnitude of the bias voltage needed to power giant magnetoresistive magnetic field sensor 36 will be the same as that used to bias magnetic field sensor 32. The cylindrical sleeve 33 is a magnetic field shield that is recessed into the inner volume of tube 40' proximate its first terminal end 41'. The cylindrical sleeve 33 is displaced linearly from the first terminal end 41' to accommodate the first placement of the magnetic field sensor 32. While the cylindrical sleeve 33 is a conductive magnetic field shield, it could have been made of dielectric material. The giant magnetoresistive magnetic field sensor 36, the applied magnetic field sensor 32, cylindrical sleeve 33 and the magnetic excitation head 31 are potted in dielectric compound 38 which displaces all the air in the volume of plastic tube 40' defined by plate 5 and a plane that is coplanar with the first terminal end 41' of tube 40' which is in turn mechanically connected to plastic hand held handle 42'. The handle 42' contains multi-pin connectors 44' and 45'. Connector 44' is used to input the control signal to bipolar power supply 28'. Connector 45' is connected to the output of signal conditioning circuitry 18' which is connected to giant magnetoresistive magnetic field sensor 36 via channel 18a' (not shown in FIG. 3} and to magnetic field sensor 32 via channel 18b' (not shown in FIG. 3). Connector 45' is also used to provide connection to analysis units, which may be a basic analog or digital analysis system equipped with software for frequency and time domain analyses. The control signal for 5 volt power supply 12' is fed through connector 45'. The oscillatory drive signal from bipolar power supply 28' used to power the electromagnet 31 is conveyed thereto by electrical leads 29'.

Mode of Operation of the Apparatus of This Invention

Figure 7:
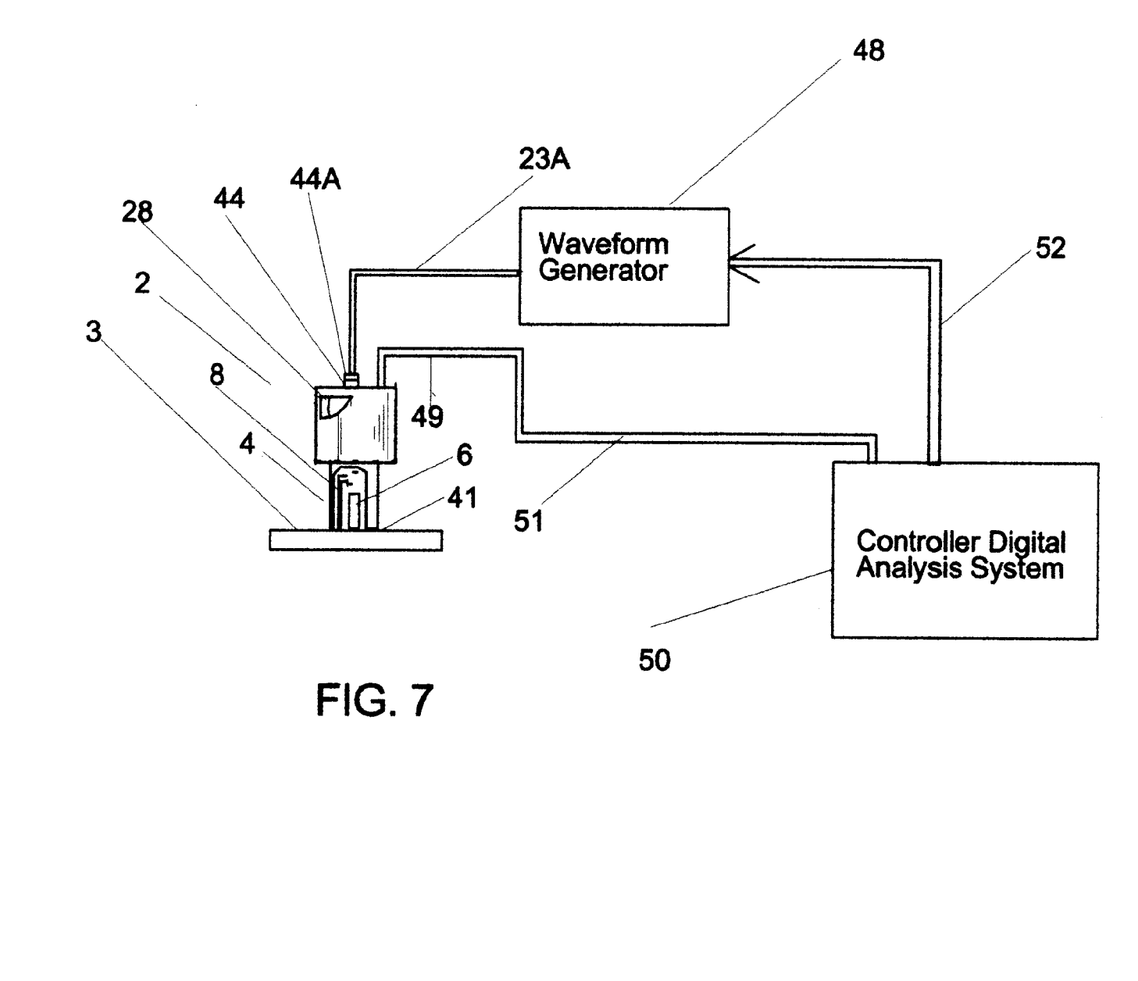
FIG. 7 is a schematic representation of the probe of this invention and ancillary equipment employed in the use of the probe.

The operation of the probe of the first embodiment of this invention will now be briefly described. It should be obvious to any one of ordinary skill in the art that the probe may be employed in various measurements where the Barkhausen phenomenon is exploited. During the development of the probe, the electromagnet 4 was driven by waveform generator 48 (see FIG. 7) coupled to commercial flat pack bipolar power supply 28. During use, the first terminal end 41 of plastic tube 40, which house the electromagnet 4 and magnetoresistive magnetic field sensor 6, is placed in contact with test sample 3. When the first terminal end 41 of the probe of the first embodiment is placed in contact with the test sample, the output of the waveform generator 48, which is connected to bipolar power supply 28 via cable 49, female connector 44a and male connector 44, was varied manually causing a variable magnetic field to be applied to ferromagnetic sample 3. In the testing of the probe of the first embodiment, the variable magnetic field was applied manually. The control of the variable magnetic field could have been applied either manually or automatically, as by digital controller/analysis unit 50 of FIG. 7, which is connected to waveform generator 48 via control cable 52. The Barkhausen signal generated by the variable magnetic field was detected by the giant magnetoresistive magnetic field sensor 6 whose output pulses were amplified by instrumentation amplifier 19a and fed to low noise high gain bandwidth amplifier 21a whose output was fed to bandpass filter 23. The output of the bandpass filter 23 was fed to ordinary digital controller/analysis unit 50 of FIG. 7 via cable 51 where it is analyzed or stored for offline analyses. The ordinary digital controller/analysis unit 50 is equipped with a digital-to-analog electronic capability. The method and choice of analysis of the output pulses of sensor 6, depending on the objective of the measurement, are independent of the manner in which the signals are derived. For example, if one is interested in determining the easy axis of magnetization in a steel sample, a simple true RMS digital voltmeter may be used. For more detailed analyses, time domain and frequency domain analyses of the voltage pulses may performed using well known algorithms (e.g., Fast Fourier Transforms, R.M.S. and real time peak detection algorithms). The complexity of the analysis unit may vary considerably depending on the goal of the measurement program in which the probe is used.

The Barkhausen probes of the first and second embodiments of this invention are described as cylindrical handheld probes for use with portable and non-portable analysis equipment in nondestructive testing of ferromagnetic specimens. It could, however, have one of many different three-dimensional shapes with an array of Barkhausen probes with onboard or remote analysis and readout components.

Other variations will be readily apparent to those of ordinary skill in the art. The foregoing is not intended to be an exhaustive list of modifications but rather is given by way of example. It is understood that it is in no way limited to the above embodiments, but is capable of numerous modifications within the scope of the following claims.

Having thus described the aforementioned invention, we claim:

1. A Barkhausen probe, with a plastic housing, for performing non-destructive evaluation of conductive materials, said probe comprising:

at least one magnetic field generating means, comprising an electromagnet having a U-shaped core made of magnetizeable material with conductive wire coiled around a portion of said U-shaped core for applying a magnetic field to said conductive materials;

at least one giant magnetoresistive material based sensor mounted in a cylindrical magnetic field shield such that the easy axis of said at least one giant magnetoresistive material based sensor is collinear with the central axis of said cylindrical magnetic field shield with the system of the giant magnetoresistive material based sensor and cylindrical magnetic field shield symmetrically straddled by said U shaped electromagnet in a manner so as to make the giant magnetoresistive material based sensor responsive to fluctuating magnetic signals induced in conductive materials by said magnetic fields generating means and essentially non-responsive to magnetic fields not originating in the conductive material;

means, in communication with said at least one giant magnetoresistive material based sensor, for conditioning the output pulses from the giant magnetoresistive material based sensor resulting from said fluctuating magnetic signals incident thereupon and providing conditioned output signals for analysis;

means connected to the output of said means for conditioning the output pulses from the giant magnetoresistive material based sensor for collecting and analyzing the conditioned output signals.

2. A probe according to claim 1, wherein said means for collecting and analyzing the conditioned output signals of the giant magnetoresistive material based sensor consist of a digital controller and an analysis system.

3. The probe of claim 2, wherein said analysis system is equipped with time and frequency domain algorithms for Fast Fourier Transforms, R.M.S. and real time peak detection analyses.

4. The probe according to claim 1 wherein said means, in communication with said at least one giant magnetoresistive material based sensor for conditioning the output pulses from the giant magnetoresistive material based sensor comprises:

at least one instrumentation amplifier for conditioning the output pulses from the giant magnetoresistive material based sensor;

at least one low noise amplifier electrically connected to the output of said instrument amplifier for amplifying the output of the instrumentation amplifier; and, at least one bandpass filtering means electrically communicating with said low noise amplifier for eliminating unwanted noise from the output of the low noise amplifier.

5. The probe of claim 1, wherein said giant magnetoresistive material based sensor comprises four magnetoresistive material based elements arranged in a Wheatstone bridge configuration.

6. The probe of claim 5, wherein at least two of said four magnetoresistive material based elements are used to detect the Barkhausen induced noise in the material under nondestructive evaluation.

7. The probe of claim 5, wherein at least one of the four magnetoresistive material based elements is used to indirectly monitor the strength of the magnetic field applied to the material under investigation.

8. An apparatus having a tubular first terminal end for measuring Barkhausen noise signals, comprising:

a u-shaped electromagnet for inducing a magnetic field into a ferromagnetic material;

a hollow cylindrical magnetic field shield positioned between the opposing legs of said u-shaped electromagnet;

a solid state sensor in a Wheatstone Bridge circuit configuration, whose four elements consist of giant magnetoresistive material based elements configured to maximize the sensitivity of said solid state sensor to Barkhausen noise by positioning the sensor within the interior of said hollow cylindrical magnetic field shield with its easy axis collinear with the central axis of the hollow cylindrical magnetic field shield;

a magnetic field sensor positioned proximate the first terminal end of said apparatus for measuring Barkhausen noise;

two separate channels of signal conditioning means connected to said solid state sensor in a Wheatstone bridge circuit configuration and to said magnetic field sensor for conditioning the voltage output therefrom each of said two separate channels comprising: an instrumentation amplifier; a high gain bandwidth amplifier; and a bandpass filter; electrically connected operationally in sequence as listed and terminate with electrical connections to means for connecting to control and analysis means;

electrical power means for powering the electromagnet, the solid state sensor in a Wheatstone bridge circuit configuration and the magnetic field sensor; and, integral housing means for operably enclosing the electromagnet, the cylindrical hollow magnetic field shield, the solid state sensor in a Wheatstone bridge circuit configuration and the magnetic field sensor, and the signal conditioning means and the electrical power means.

9. The apparatus of claim 8, wherein said integral housing means comprises mechanically connected tubular plastic units.

10. A tubular housed apparatus having one active end for generating and detecting Barkhausen noise signals, said apparatus comprising:

at least one magnetic field generation means which consists of an electromagnet cooperating with a bipolar power supply driven between its various polarities via a waveform generator; and, at least one giant magnetoresistive material based sensor surrounded by one hollow cylindrical magnetic shield with said giant magnetoresistive material based sensor and hollow cylindrical magnetic shield assembled such that their central axes are collinear and symmetrically located proximate to said magnetic field generator means in said active end of said apparatus where they are held fixed by potting means in said tubular housing.

11. The apparatus of claim 10, wherein the said at least one giant magnetoresistive sensor is potted using a dielectric with its sensitive axis collinear with the central axis of said hollow cylindrical magnetic shield.

12. The apparatus of claim 10, wherein the said at least one giant magnetoresistive sensor is potted with its sensitive axis orthogonal to the central vertical axis of said hollow cylindrical magnetic shield.

13. The apparatus of claim 10, wherein the said at least one cylindrical sleeve consists of dielectric material.

14. The apparatus of claim 11, wherein the said at least one cylindrical sleeve consists of mu-metal or another magnetic shielding material.

15. The apparatus of claim 1, wherein the said at least one giant magnetoresistive sensor is potted with its sensitive axis orthogonal to the central vertical axis of said hollow cylindrical magnetic shield.

16. The apparatus of claim 1, wherein the said at least one giant magnetoresistive sensor is potted with its sensitive axis orthogonal to the central vertical axis of hollow cylindrical dielectric sleeve.

* * * * *